United States Patent [19]
Yamada et al.

[11] Patent Number: 4,806,692
[45] Date of Patent: * Feb. 21, 1989

[54] PROCESS FOR PRODUCING AN OXYGEN-CONTAINING ORGANIC COMPOUND FROM OLEFINS

[75] Inventors: Mutsuo Yamada; Taiji Kamiguchi; Hirotoshi Tanimoto, all of Kure; Yoshijiro Arikawa, Yokohama; Hiroyuki Kaku, Hiroshima; Shigehito Takamoto, Kure, all of Japan

[73] Assignee: Babcock-Hitachi Kabushiki Kaisha, Tokyo, Japan

[*] Notice: The portion of the term of this patent subsequent to Aug. 12, 2003 has been disclaimed.

[21] Appl. No.: 820,004

[22] Filed: Jan. 21, 1986

[30] Foreign Application Priority Data

Jan. 21, 1985 [JP] Japan .................................. 60-8862
Feb. 13, 1985 [JP] Japan .................................. 60-24430

[51] Int. Cl.$^4$ ............................................ C07C 45/33
[52] U.S. Cl. .................... 568/401; 568/478; 568/360; 568/357
[58] Field of Search ................ 568/401, 360, 357, 478

[56] References Cited

U.S. PATENT DOCUMENTS 4,155,879  5/1979  Mimoun et al. ...................... 568/401
4,605,776  8/1986  Kamiguchi et al. ................. 568/401
4,620,038  10/1986 Tanimoto et al. ................... 568/401

Primary Examiner—James H. Reamer
Attorney, Agent, or Firm—Fay, Sharpe, Beall, Fagan, Minnich & McKee

[57] ABSTRACT

A process for producing an oxygen-containing organic compound by oxidizing olefins under milder conditions is provided, which process comprises oxidizing an olefin activated by its complex formation, in the presence of a platinum group metal complex capable of forming an olefin complex through coordination of the platinum group metal with said olefin, and also in the presence of water, and further oxidizing and regenerating the resulting reduced platinum group metal complex with oxygen coordinated with a transition metal and activated thereby.

21 Claims, 3 Drawing Sheets (1) OXIDATION OF $C_2H_4$ WITH PD(2)
(2) OXIDATION OF PD(O) WITH CU(2) AND REGENERATION OF PD(2)
(3) OXIDATION AND REGENERATION FROM CU(1) TO CU(2) WITH $O_2$

PRIOR ART (3 STEPS, PD(2)/PD(O)/ CU(2)/CU(1) REDOX PROCESS)

(1) OXIDATION OF $C_2H_4$ WITH PD(2)
(2) OXIDATION OF PD(O) WITH $O_2$ COMPLEX AND REGENERATION OF PD(2)

PRESENT INVENTION (2 STEPS)

(1) OXIDATION OF CYCLOPENTENE WITH PD(2)
(2) OXIDATION OF PD(O) WITH $O_2$ COMPLEX AND REGENERATION OF PD(2)

PRESENT INVENTION (2 STEPS)

(1) OXIDATION OF CYCLOPENTENE WITH PD(2)
(2) OXIDATION OF PD(O) WITH CU(2) AND REGENERATION OF PD(2)
(3) OXIDATION AND REGENERATION FROM CU(I) TO CU(2) WITH $O_2$

PRIOR ART (3 STEPS, PD(2)/PD(O)/ CU(2)/CU(I) REDOX PROCESS)

PROCESS FOR PRODUCING AN OXYGEN-CONTAINING ORGANIC COMPOUND FROM OLEFINS

BACKGROUND OF THE INVENTION

1. Field of the Invention

This invention relates to a process for producing an oxygen-containing organic compound from olefins, and more particularly it relates to a process for producing an oxygen-containing organic compound by oxidizing olefins using a platinum group complex in the presence of water and an oxygen complex.

2. Description of the Prior Art

As an oxidation reaction for various olefins which has so far been commercially carried out, there is famous Hoechst-Wacker process (Japanese patent publication Nos. 36-1475/1961 and 36-7869/1961). According to the process, a composite catalyst having $Pd(2)Cl_2$ and $Cu(2)Cl_2$ as catalyst components dissolved in a hydrochloric acid solution (pH: 0 to 2) has been used. Description will be made for example referring to ethylene oxidization reaction. First, ethylene is oxidized by means of divalent palladium and water to form acetaldehyde. The reaction is expressed by the following equation:

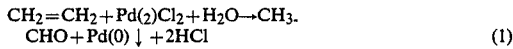

$$CH_2=CH_2+Pd(2)Cl_2+H_2O \rightarrow CH_3\text{-}CHO+Pd(0)\downarrow +2HCl \quad (1)$$

As seen from the reaction equation, Pd(2) is reduced into metallic paradium (Pd(0)) which precipitates. Thus, by making $Cu(2)Cl_2$ coexistent therewith in a large quantity, it is necessary to oxidize and regenerate Pd(0) into Pd(2) as shown in the following equation:

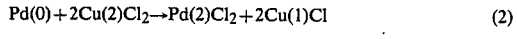

$$Pd(0)+2Cu(2)Cl_2 \rightarrow Pd(2)Cl_2+2Cu(1)Cl \quad (2)$$

Difficulty soluble Cu(1)Cl by-produced at that time is oxygen-oxidized in the coexistence of HCl and returned into $Cu(2)Cl_2$ according to the following equation:

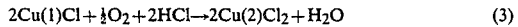

$$2Cu(1)Cl + \tfrac{1}{2}O_2 + 2HCl \rightarrow 2Cu(2)Cl_2 + H_2O \quad (3)$$

By employing a redox system of Pd(2)/Pd(0) and Cu(2)/Cu(1) in such a manner, continuous oxidation of ethylene has been made possible, but this oxidation is not a direct oxidation of ethylene with oxygen, but an oxidation by means of Pd(2) ion dissolved in water; hence the oxidation and regeneration of Cu(1)Cl becomes a rate-determining step. Further, since the solubility of oxygen in water is low, it must be raised up and therefor the oxygen treatment has been carried out at high temperatures and high pressures such as 100° C. and 10 atm. Further, in the case of higher olefins, since the oxidation rate is low as to need a longer reaction time, it has been regarded that oxidation of 1-butene or higher olefins has not yet been practically carried out (Tamura, "Catalyst", 21, 167 (1979)). Still further, since a high concentration of HCl aqueous solution is used, a corrosion-resistant material such as titanium, Hastelloy (tradename of product made by Heynes Stellite Co., Ltd.) is required. Thus, the reaction has been carried out at high temperatures and high pressures as described above, so that a process capable of oxidizing olefins under mild conditions has been desired.

On the other hand, as to cyclic compounds, cyclopentanone as a representative example of ketocycloparaffins is a useful compound, since it is readily convertible into δ-valerolactone which, when subjected to ring opening polymerization at room temperature, yields nylon-6,10, or sebacic acid which, when subjected to its polycondensation with hexamethylenediamine, yields nylon-6,10. Cyclopentene as its raw material is contained in a $C_5$ fraction in a mixture obtained by naphtha cracking in a high concentration in the range of 15 to 25% by weight, or it is easily obtained by partial hydrogenation of cyclopentadiene by-produced in a proportion of 2 to 4% at the time of ethylene production (see K. Weissermel and H. J. Arpe, Industrial Organic Chemistry, translated by Mitsuaki Mukohyama, Tokyo Kagaku Dohjin (1978)). Accordingly, if oxidation reaction of cyclopentene into cyclopentanone is commerciallized, this will have a great meaning.

According to a cyclopentanone production process via cyclopentene oxidation, which has so far been reported, first the reaction is carried out at a reaction temperature of 50° C., for a reaction time of 2 hours in the presence of a catalyst system of palladium chloride (hereinafter denoted by $Pd(2)Cl_2$) and ferric chloride ($FeCl_3.6H_2O$) in ethanol solvent, to obtain the product with a conversion of 70% and a selectivity of 90%, but the reaction mechanism has not yet been known (Takehira et al, Japan Chemical Society, the 45th Spring Annual Meeting, 4G 19 (1983)).

On the other hand, it has already been reported by F. C. Phillips in 1984 that various olefins are oxidized by means of $Pd(2)Cl2$ in the presence of water the form oxygen-containing compounds (F. C. Phillips, J. Am. Chem. Soc., 16, 255 (1984)). As to this reaction, since such compounds are prepared in the same manner as in the case of linear olefins described above with regard to Hoechst-Wacker process, the above-mentioned problems of corrosion-resistance and reaction being carried out at high temperatures and high pressures has still been raised.

The object of the present invention is to provide a process for producing an oxygen-containing organic compound having overcome the above-mentioned problems, by oxidizing olefins under milder conditions.

The present inventors have previously proposed a process for producing acetaldehyde in a non-aqueous solution system under mild conditions, by directly oxidizing ethylene activated by complex formation, with combined oxygen activated by complex formation, in the presence of a composite catalyst comprising a transition metal complex capable of forming an oxygen complex through coordination of the transition metal with oxygen and a platinum group complex capable of forming an ethylene complex through coordination of the platinum group metal with ethylene (Japanese patent application Nos. 58-104291/1983 and 59-4180/1984).

The present invention is based on such a finding made during the above research, that the oxygen complex in the above-mentioned inventions has a capability of oxidizing Pd(0) into $Pd(2)Cl_2$ in the presence of water with a good efficiency.

SUMMARY OF THE INVENTION

The present invention resides in a process for producing an oxygen-containing organic compound in a water-containing mixed solvent system under mild conditions, which process comprises oxidizing an olefin activated by its complex formation, in the presence of a platinum group metal complex capable of forming an olefin complex through coordination of the platinum group metal with said olefin, and also in the presence of water, further oxidizing and regenerating the resulting reduced platinum group metal complex with oxygen coordinated with a transition metal and activated thereby.

The present invention is more concretely as follows:

In the process for producing an oxygen-containing organic compound by oxidizing an olefin in the presence of a metallic catalyst, the improvement which comprises as the catalyst components, a composite catalyst comprising a metallic complex ($M_mX_n.L_l$) capable of forming an oxygen complex by coordination thereof with oxygen, and a metallic complex ($M'_{m'}X_{n'}.L'_{l'}$) capable of forming an olefin complex by coordination thereof with said olefin, and water, said M being a transition metal belonging to group I, groups IV-VII or iron group of group VIII of the Periodic Table, said X being at least one anion selected from the group consisting of $Cl^-$, $Br^-$, $I^-$, $BF_4^-$, $PF_4^-$, $CH_3COO^-$ and $SO_4^{2-}$, said L as a ligand being an organic phosphorus compound or a nitrile, said L' as a ligand being at least one compound selected from the group consisting of nitriles, organic fluorine compounds and organic phosphorus compounds, said M' being a transition metal belonging to platinum group of group VIII of the Periodic Table, said m, m' n and n' each being a constant to be determined by balance of the valences of said transition metals and said anion, and said l and l' each being a number of coordination.

DESCRIPTION OF PREFERRED EMBODIMENTS

The present invention will be described referring to a representative example.

An oxygen complex (($Cu(1)Cl.hmpa)_2.O_2$) formed from a complex ($Cu(1)Cl.hmpa$) of Cu(1)Cl with tris(dimethylamino)phosphine oxide (another name: hexamethylphosphoroamide; hereinafter denoted by hmpa) is reacted with e.g. an ethylene complex ($Pd(2)Cl_2.PhCN.C_2H_4$) of a complex ($Pd(2)Cl_2$ PhCN.hmpa) formed from $Pd(2)Cl_2$ and hmpa and benzonitrile (PhCN) in the presence of water, and the reaction is presumed to proceed in the following reaction mechanism:

(a) Formation of ethylene complex and oxidation of ethylene:

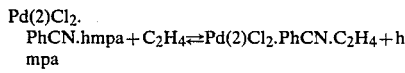  (4)

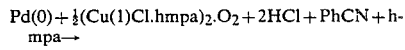
  (5)

(b) Regeneration of Pd(0):

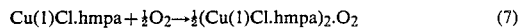

$Pd(2)Cl_2.PhCN.hmpa + Cu(1)Cl.hmpa + H_2O$  (6)

(c) Regeneration of oxygen complex:

$Cu(1)Cl.hmpa + \frac{1}{2}O_2 \rightarrow \frac{1}{2}(Cu(1)Cl.hmpa)_2.O_2$  (7)

Figure 2:
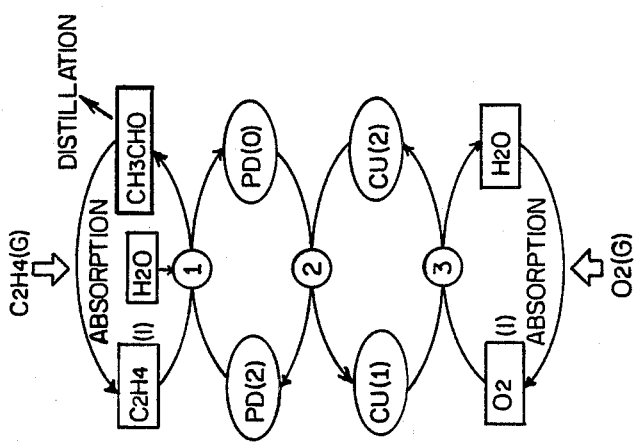
FIG. 2 shows a figure illustrating the process of the prior art (Pd(2)/Pd(0) and Cu(2)/Cu(1) redox process) in a model manner.
Figure 1:
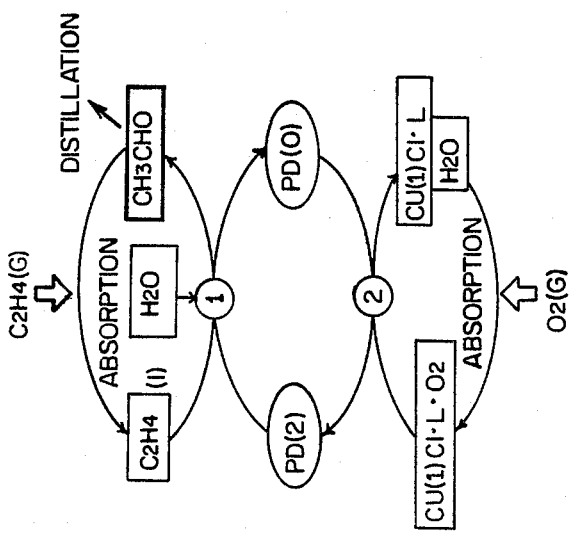
FIG. 1 shows a figure illustrating the process of the present invention in a model manner.
Figure 3:
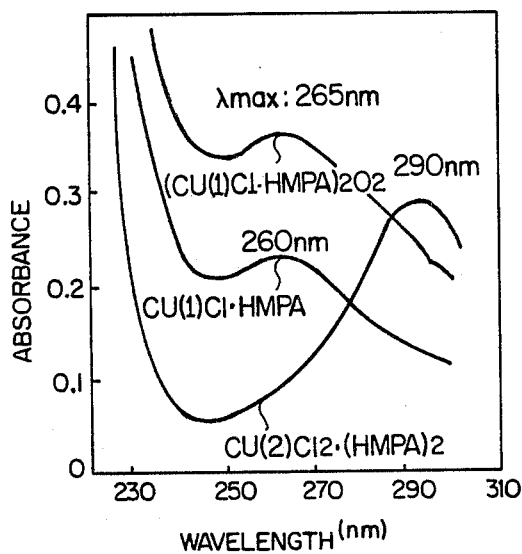
FIG. 3 shows a chart illustrating the ultraviolet absorption spectra of a complex used in the present invention.

FIG. 1 shows the catalyst cycle of the present invention in a model manner, and it will be understood that the process is entirely different from Hoechst-Wacker process. Further, as described above, FIG. 3 shows the ultraviolet absorption spectra directed to the complex used in the present invention, and FIG. 4 shows a chart of comparison of change with time in the quantity of Pd(0) oxidized with the oxygen complex in the present invention with that in the quantity of Pd(0) oxidized with $CuCl_2$ in the Wacker process.

Further, the specific features of the above respective reactions will be described in more detail.

Figure 4:
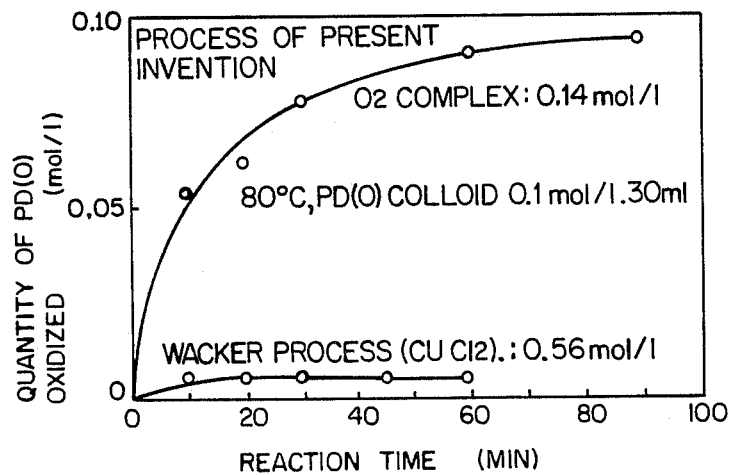
FIG. 4 shows a chart wherein change with time in the quantity of Pd(0) oxidized with the $O_2$ complex in the present invention is compared with that in the quantity of Pd(0) oxidized with $CuCl_2$ in the Wacker process.

The rate of the oxidation-regeneration of Pd(0) into $Pd(2)Cl_2$ complex at 80° C., shown in the above equation (6), was about 10 times the rate with the above $Cu(2)Cl_2$ (see the equation (2)), as seen in FIG. 4.

In addition, if the complex which forms the oxygen complex as described above is expressed by the formula $M_nX_n.L_lCu(1)Cl.hmpa$ corresponds to a case where m=1, n=1 and l=1. Further, for example, if Ti(3) or V(3) is made a central metal and the anion is made $Cl^-$, the resulting complex is $Ti(3)Cl_3.hmpa$ or $V(3)Cl_3.hmpa$ which corresponds to a case where m=1, n=3 and l=1.

Now, $Cu(1)Cl.hmpa$, as shown in the above equation (7) selectively absorbs oxygen from air and is returned to the original oxygen complex, and the rate at 80° C. is about 8 times the rate of the above-mentioned re-oxidation reaction of $Cu(1)Cl$ with oxygen into $Cu(2)Cl_2$ (the above equation (3)).

Thus, when the above ethylene is activated by forming an ethylene complex and reacted in the presence of water, acetaldehyde can be produced from ethylene efficiently. Thus we have made extensive research about various platinum group metal complexes, and as a result, have found that as a representative example, when $Pd(2)Cl_2$ has PhCN, as a modifying ligand further added besides the above hmpa, the following new complex consisting of mixed ligands was formed:

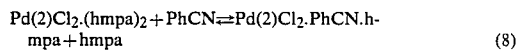  (8)

In addition, when this complex is expressed by the formula $M'_{m'}X_{n'}.L'_{l'}$, then m'=1, n'=2 and l'=1.

This new Pd(2) complex forms, for example, an ethylene complex with ethylene according to the equation (4), and since ethylene is notably activated in the resulting ethylene complex, the oxidation reaction with Pd(2) in the complex (the equation (5)) proceeds readily whereby it is possible to prepare acetaldehyde under mild conditions and in a single step.

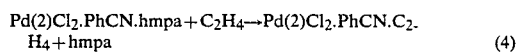  (4)

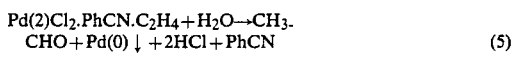

The resulting Pd(0) is easily returned by means of the oxygen complex into the original Pd(2)Cl$_2$ complex.

In the case of producing a ketocycloparaffin from a cycloolefin, too, the reaction proceeds in the following mechanism:

(a) Formation of cyclopentene complex and formation of cyclopentanone by oxidation of cyclopentene:

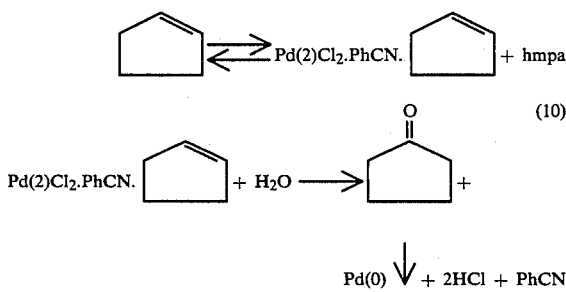

(b) Regeneration of Pd(0):

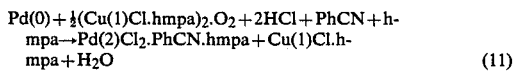

(c) Regeneration of O$_2$ complex:

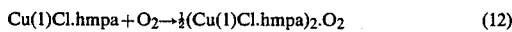

Figure 5A:
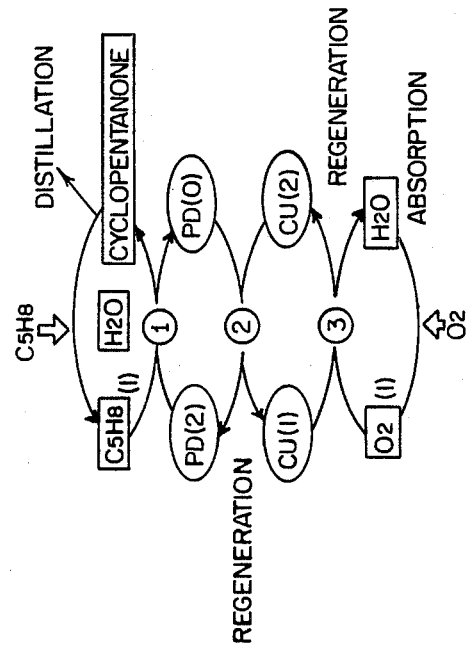
FIG. 5 (A), (B) show figures illustrating the present invention as the synthesis of cyclopentanone in a model manner as compared with the Wacker process.
Figure 5B:
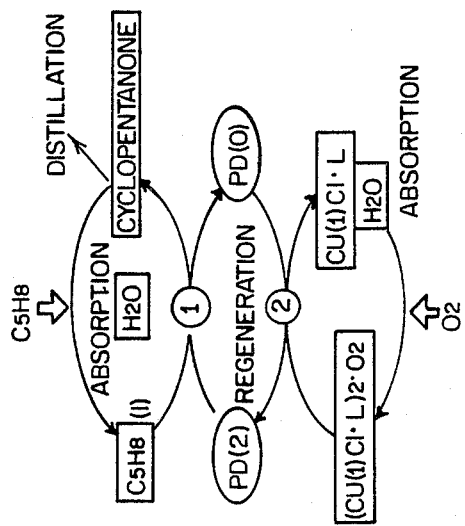

FIG. 5 (A) shows the cycle of the present reaction so as to be readily understandable and in a model manner, which cycle is entirely different from that of Hoechst-Wacker process (see FIG. 5 (B)).

The specific features of the respective reactions are almost the same as those in the above-mentioned case of producing acetaldehyde from ethylene; hence the description of the specific feature is omitted here.

In the present invention, olefin is activated in the form of its complex, followed by oxidizing olefin by means of the oxidative force of Pd(2) and oxidizing and regenerating the resulting Pd(0) with oxygen activated in the oxygen complex, as described above; hence it is possible to produce corresponding oxygen-containing organic compound under mild conditions such as the atmospheric pressure and 80° C. or lower, in a short time, highly selectively and with a high yield. Further since the oxygen-containing compound can be produced according to one step process, it is possible to reduce costs of the apparatus, and utility to a large extent as compared with those of the prior art.

In the composite catalyst system of the present invention, as M in M$_m$X$_n$L$_l$ as the complex catalyst capable of forming the oxygen complex, transition metals are preferable such as Cu and Ag of group I of the Periodic Table, Ti and Zr of group IV thereof, V and Nb of group V thereof, Cr, Mo and W of group VI thereof, Mn of group VII thereof and Fe and Co of group VIII thereof, etc., and among these, Cu(I), Ti(3) and V(3) are more preferable. Further, as X at least one anion selected from Cl$^-$, Br$^-$, I$^-$, BF$_4^-$, PF$^-$, CH$_3$COO$^-$, SO$_4^{2-}$, etc. are preferable, and among these, Cl$^-$, Br$^-$ and I$^-$ are more preferable. Further, preferred examples of the ligand are nitriles and organic phosphorus compounds represented by derivatives of phosphoric acid such as triphenylphosphine oxide, hexamethylphosphoroamide, etc., mono-, di- or tri-ester obtained by reaction of phosphoric acid with methanol, ethanol, etc., further, dimethyl methylphosphonate, methyl dimethylphosphonate, etc., derivatives of phosphorous acid such as mono-, di- or tri-ester obtained by reaction of phosphorous acid with methanol, ethanol, etc., phenylphosphorous acid ester, dimethylphosphinous acid ester, triethylphosphine, triphenylphosphine, etc. Among these, hexamethylphosphoroamide (hmpa) and benzonitrile (PhCN) are particularly preferable.

On the other hand, as M' in the complex catalyst (M'$_{m'}$X$_{n'}$·L'$_{l'}$) capable of forming the olefin complex, transition metals belonging to Pt group of group VIII of the Periodic Table, particularly Pd and Pt, are preferable. Further, as the ligand L', nitriles such as acetonitrile, propionitrile, benzonitrile, tolunitrile, etc. and the above-mentioned organic phosphorus compounds and further, organic fluorine compounds such as fluorinated toluene, benzotrifluoride, etc. are preferable. Among these, nitriles are particularly preferable.

In the formula of the above complex catalysts, m, m', n, n', l and l' are each selected from numbers of 1 to 4.

In order to carry out the reaction of the present invention in solution state, a suitable solvent for dissolving the complex capable of forming the oxygen complex and the complex capable of forming an olefin complex may be used, and such a solvent is at least one compound selected from the group consisting of aliphatic, alicyclic or aromatic hydrocarbons, oxygen-containing organic compounds, organic halogen compounds, nitrogen-containing compounds, organic sulfur compounds, organic fluorine compounds and heterocyclic compounds and when L and L' as ligands are liquid, these ligands per se are used as the solvent at the same time with the role of ligands.

Concretely, in the case of a linear olefin, various solvents such as heptane, toluene, methylcyclohexane, dioxane, ethylene carbonate, propylene carbonate, methyl isobutyl ketone, ethylene glycol, ethanol, chlorobenzene, N-methylpyrrolidone, tetrahydrofuran, ethers e.g. ethylene glycol dibutyl ether, diethylene glycol monomethyl ether, etc., or mixtures of the foregoing may be used, and when the ligands L or L' are liquid, these may be used as solvent at the same time with the role of ligands.

Referring to the case of cyclopentene, preferable solvents are those which dissolve the composite catalyst and at the same time are easy in separation from the resulting cyclopentanone (b.p.: 131° C./760 mmHg), reduce the viscosity of the catalyst solution and promote the mass transfer. As such solvents, at least one selected from various solvents such as methylcyclohexane, methyl isobutyl ketone, ethylene glycol, dioxane, ethylene carbonate, chlorobenzene, N-methylpyrrolidone, ethers e.g. ethylene glycol dibutyl ether, ethylene glycol monomethyl ether, etc., or mixtures of the foregoing may be used, and when the ligands L or L' are liquid, these may be used as solvent at the same time with the role of ligands.

In the case of cyclohexene, too, preferable solvents are those which dissolve the composite catalyst and at the same time is easy in separation from the resulting cyclohexanone (b.p.: 156° C./760 mmHg), reduce the viscosity of the catalyst solution and promote the mass transfer. As such solvents, at least one selected from various solvents such as heptane, toluene, methylcyclohexane, methyl isobutyl ketone, ethanol, ethylene glycol, dioxane, ethylene carbonate, chlorobenzene, N-methylpyrrolidone, tetrahydrofuran, ethers e.g. ethylene glycol dibutyl ether, diethylene glycol monomethyl ether, etc. or mixtures of the foregoing may be used, and when the ligands L or L' are liquid, these may be used as solvent at the same time with the function of ligand.

Further, in order to enhance the selectivity and yield of the reaction, it is preferred, as shown in Examples mentioned later, to make a basic (electrondonating) compound coexistent with the reaction system, such as sulfolane, dimethylsulfolane, dimethylsulfoxide, dimethylformamide, trimethylmethane, dimethylsulfone, etc.

According to the present invention, an olefin coordinated with a platinum group metal complex and activated thereby is oxidized by means of a specified composite catalyst system, without direct contact of the olefin gas with oxygen gas, and further, the resulting reduced platinum group metal is oxidized by oxygen coordinated with a transition metal complex and activated thereby; thus the reaction can be carried out under the atmospheric pressure and in the vicinity of room temperature to produce corresponding oxygen-containing organic compounds with a high selectivity and with a high efficiency.

In the present invention, even when air is used as an oxygen source, oxygen is selectively absorbed so that the same effectiveness as that in the case where pure oxygen gas is used can be obtained. Further, since the oxygen absorption is irreversible, it is possible to easily remove excess free oxygen after the oxygen complex has been formed, which is very advantageous in the aspect of safety.

The present invention will be described in more detail by way of Examples.

EXAMPLE 1

Into a 100 ml measuring flask were fed Cu(1)Cl (35 g, 0.35 mol) and hmpa (100 g) to prepare a Cu(1)Cl. hmpa complex solution (97 ml). Further, into another 100 ml measuring flask were fed Pd(2)Cl$_2$ (1.3 g, 7.5 mmols) and PhCN (15.5 g) and hmpa (79 g) to prepare a Pd(2)Cl$_2$. PhCN.hmpa complex solution (92 ml). Both the solutions were then transferred into a 1 l reactor and sulfolane (392 g) was added thereto to prepare a catalyst solution (500 ml) containing 0.7 mol/l of Cu(1)Cl and 0.015 mol/l of Pd(2)Cl$_2$, followed by adding water (49 g, 9%) to the solution and introducing air thereinto at 30° C. under the atmospheric pressure to prepare a solution having an oxygen complex concentration of 0.145 mol/l. The solution was then heated to 40° C. and nitrogen gas was passed therethrough, but only oxygen remaining in the gas phase part of the reactor and physically dissolved oxygen were removed, and no elimination of the combined oxygen from the oxygen complex in the solution was observed, that is, the absorption reaction of oxygen was irreversible. This is very advantageous in the aspect of safety in the practical process.

EXAMPLES 2~9

Experiments were carried out as in Example 1 but under conditions described in Table 1, to obtain the quantities of CH$_3$CHO produced as shown in the rightest column of the Table, at 40° C. in 30 minutes.

TABLE 1

| Example | CuCl (M) | hmpa (M) | PdCl$_2$ (M) | PhCN (M) | ⌐⎯⎯⌐<br>SO$_2$<br>⌐⎯⎯⌐ (M) | H$_2$O (M) | O$_2$ (M) | T (°C.) | CH$_3$CHO (g) |
|---|---|---|---|---|---|---|---|---|---|
| 2 |   | 1.0 |   |   | 8.3 |   |   |   | 7.4 |
| 3 |   | 4.0 |   | 0.3 | 2.9 |   |   |   | 3.5 |
| 4 |   | 1.0 |   |   | 5.9 |   |   |   | 6.5 |
| 5 | 0.7 | 2.0 | 0.015 | 2.6 | 4.0 | 5.0 | 0.145 | 40 | 4.9 |
| 6 |   | 4.2 |   |   | 0 |   |   |   | 2.4 |
| 7 |   | 1.0 |   |   | 2.2 |   |   |   | 12.7 |
| 8 |   | 2.0 |   | 6.0 | 0.35 |   |   |   | 12.8 |
| 9 |   | 2.8 |   |   | 0 |   |   |   | 5.6 |

In view of these facts, there is a tendency that the higher the concentration of PhCN, the larger the quantity of CH$_3$CHO produced. However, in the case where the sulfolane concentration was 0 mol, the quantity of CH$_3$CHO lowered.

EXAMPLE 10

Example 8 was repeated except that PhCN was replaced by CH$_3$CN to obtain 12 g of CH$_3$CHO.

EXAMPLE 11

Example 8 was repeated except that the reaction temperature was raised from 40° C. up to 60° C. to obtain 12.8 g of CH$_3$CHO at a reaction time of 20 minutes.

EXAMPLE 12

Example 8 was repeated except that the concentration of Cu(1)Cl was decreased from 0.7 M down to 0.5 M; the PhCN concentration was decreased from 6.0 M to 5.0 M; and the O$_2$ concentration was raised from 0.35 M up to 1.4 M to obtain 12.7 g of CH$_3$CHO at a reaction time of 30 minutes.

EXAMPLE 13

Example 8 was repeated except that the quantity of water added was made 15 g (3%) to obtain 9.0 g of CH$_3$CHO in 30 minutes. Further, in a quantity of water added of 88 g (15%), 8.6 g of CH$_3$CHO was obtained in 30 minutes. In view of this Example and Example 8, it is considered that a water content in the vicinity of 9% is optimum in the present reaction system.

EXAMPLE 14

Example 8 was repeated except that Cu(1)Cl (0.7 M) was replaced by Ti(3)Cl$_3$ (0.7 M) to obtain 9 g of CH$_3$CHO in 30 minutes.

EXAMPLE 15

Example 8 was repeated except that Cu(1)Cl (0.7 M) was replaced by V(3)Cl$_3$ (0.7 M) to obtain 9.6 g of CH$_3$CHO in 30 minutes.

EXAMPLE 16

Example 8 was repeated except that Pd(2)Cl$_2$ (0.015 M) was replaced by Pt(2)Cl$_2$ (0.015 M) to obtain 12 g of CH$_3$CHO in 30 minutes.

EXAMPLE 17

The catalyst solution of Example 8 was kept at 40° C. and a mixed gas of air (20%) and ethylene (80%) was passed at a flow rate of 0.2 l/min. for 30 minutes to obtain 0.7 g of CH$_3$CHO.

EXAMPLES 18~29

Exaple 1 was repeated except that ethylene was replaced by propylene and the reaction temperature (40° C.) was replaced by 60° C. to obtain quantities of CH$_3$COCH$_3$ produced shown in the rightest column of Table 2, in 30 minutes.

TABLE 2

| Example | CuCl (M) | hmpa (M) | PdCl$_2$ (M) | PhCN (M) | SO$_2$ (M) | H$_2$O (M) | O$_2$ (M) | T (°C.) | (CH$_3$)$_2$CO (g) |
|---|---|---|---|---|---|---|---|---|---|
| 18 | | 0.2 | | | 9.8 | | | | 4.7 |
| 19 | | 2.0 | | 0.3 | 6.5 | | | | 4.1 |
| 20 | | 4.0 | | | 2.9 | | | | 10.6 |
| 21 | | 1.0 | | | 5.9 | | | | 12.4 |
| 22 | | 2.0 | | 2.6 | 4.0 | | | | 10.8 |
| 23 | 0.7 | 4.3 | 0.015 | | 0 | 5.0 | 0.145 | 60 | 3.1 |
| 24 | | 0.05 | | | 5.05 | | | | 10.0 |
| 25 | | 1.0 | | 5.0 | 3.3 | | | | 16.1 |
| 26 | | 2.0 | | | 1.4 | | | | 16.2 |
| 27 | | 1.0 | | | 2.2 | | | | 16.3 |
| 28 | | 2.0 | | 6.0 | 0.35 | | | | 16.5 |
| 29 | | 2.8 | | | 0 | | | | 7.4 |

EXAMPLE 30

Example 28 was repeated except that the quantity of CuCl was raised from 0.7 M up to 1 M to obtain 9 g of acetone at a reaction time of 5 minutes. When the concentration of Cu(1)Cl is raised at a specified O$_2$ concentration, the oxidation rate increases.

EXAMPLES 31~41

Example 1 was repeated except that ethylene was replaced by 1-butene in order to obtain methylethylketone (MEK), the reaction temperature was raised from 40° C. up to 60° C., and the reaction time was decreased from 30 minutes down to 20 minutes to obtain results shown in Table 3.

TABLE 3

| Example | CuCl (M) | hmpa (M) | PdCl$_2$ (M) | PhCN (M) | SO$_2$ (M) | H$_2$O (M) | O$_2$ (M) | T (°C.) | MEK (g) |
|---|---|---|---|---|---|---|---|---|---|
| 31 | | 1.0 | | | 8.3 | | | | 7.8 |
| 32 | | 2.0 | | 0.3 | 6.5 | | | | 6.1 |
| 33 | | 0.2 | | | 7.3 | | | | 7.7 |
| 34 | | 1.0 | | | 5.9 | | | | 7.7 |
| 35 | | 1.5 | | 2.6 | 4.9 | | | | 11.8 |
| 36 | 0.7 | 2.0 | 0.015 | | 4.0 | 5.0 | 0.145 | 60 | 11.1 |
| 37 | | 3.0 | | | 2.2 | | | | 9.0 |
| 38 | | 4.2 | | | 0 | | | | 6.3 |
| 39 | | 0.05 | | | 3.9 | | | | 5.7 |
| 40 | | 1.5 | | 6.0 | 1.3 | | | | 18.1 |
| 41 | | 2.0 | | | 0.35 | | | | 20.3 |

EXAMPLE 42

Example 41 was repeated except that CuCl (0.7 M) was replaced CuCl (0.5 M); O$_2$ (0.145 M) was replaced by O$_2$ (0.125 M); PhCN (6 M) was replaced by PhCN (5 M); and sulfolane (0.35 M), was replaced by its 1.4 M to obtain 17.5 g of MEK.

EXAMPLE 43

Example 8 was repeated except that ethylene was replaced by 1-pentene and the reaction (40° C.) was replaced by 60° C. to obtain 15 g of 2-pentanone at a reaction time of 10 minutes.

EXAMPLE 44

Example 43 was repeated except that Cu(1)Cl was replaced by TiCl(3)Cl$_3$ or V(3)Cl$_3$ to obtain 10 g and 11 g of 2-pentanone, respectively.

EXAMPLE 45

Example 43 was repeated except that Cu(1)Cl (0.7 M), PhCN (6 M) and sulfolane (0.35 M) were replaced by 0.5 M, 5M and 1.4 M, respectively to obtain 13.5 g of 2-pentanone.

EXAMPLE 46

1-Hexene (4.2 g, 50 mmols) was dissolved in the catalyst solution of Example 8, followed by carrying out the same operation as in Example 1 to prepare an oxygen complex (0.145 mol/l), and keeping the reaction temperature at 60° C. to obtain 4 g of 2-hexanone at a reaction time of 10 minutes.

EXAMPLE 47

Example 46 was repeated except that 1-hexene was replaced by 1-heptene (4.9 g) and the reaction time was kept at 80° C. to obtain 5.1 g of 2-heptanone at a reaction time of 10 minutes.

EXAMPLE 48

Example 46 was repeated except that 1-hexene was replaced by 1-octene (5.6 g, 50 mmols) and the reaction time was kept at 80° C. to obtain 6.3 g of 2-octanone at a reaction time of 10 minutes.

From the above results it can be seen that the catalyst solution of the present invention is very effective for oxidizing higher olefins.

EXAMPLE 49

Beads of macroreticulate type styrene-divinylbenzene copolymer (particle diameter 1 mm$\phi$, specific surface area 700~800 m$^2$/g) (50 ml) were impregnated with the catalyst solution containing the oxygen complex having a composition shown in Example 8, followed by suction-filtration to prepare a granular catalyst, which was then filled in a hard glass reactor having an inner diameter of 20 mm, heating to 60° C., passing ethylene at a rate of 1l/min. (SV=1200 h$^{-1}$) and analyzing acetaldehyde in the exit gas. As a result, the product was acetaldehyde, alone, and its yield based on ethylene was 60% since the reaction start till lapse of 30 minutes. Thereafter the exit gas was recycled to obtain an acetaldehyde yield based on the combined oxygen in the oxygen complex of 90%. Further, ethylene feed was once stopped and air was passed to regenerate the combined oxygen consumed by the reaction, followed by again carrying out the oxidation experiment under the above conditions, to obtain similar results.

From the foregoing, it has been clarified that even when the complex catalyst of the present invention is supported on a carrier, the present oxidation reaction by way of the combined oxygen in the oxygen complex proceeds.

In addition, as the carrier, it is possible to use a porous carrier such as silicates, active carbon porous glass, etc., and as the treating method after the above impregnation, it has been confirmed that various methods such as passing of heated gas, low temperature calcination, etc. may be employed besides the above suction-filtration.

Next, preparation examples of cyclopentanone and cyclohexanone will be described in detail.

Examples 50~64 are directed to cyclopentanone preparation and Examples 65~72, to cyclohexanone preparation.

EXAMPLE 50

Into a 100 ml capacity measuring flask were fed Cu(1)Cl (35 g, 0.35 mol) and hmpa (100 g) to prepare a Cu(1)Cl.hmpa complex solution (97 ml). Further, into another 100 ml capacity measuring flask were fed Pd(2)Cl$_2$ (1.3 g, 7.5 mmol) and pHCN (15.5 g) and hmpa (79 g) to prepare a Pd(2)Cl$_2$ PhCN.hmpa complex solution (92 ml). Both the solutions were then transferred into a 1 l reactor and sulfolane (192 g) was added thereto to prepare a catalyst solution (500 ml) containing 20.7 mols/l of Cu(1)Cl and 0.015 mol/l of Pd(2)Cl$_2$, followed by adding water (49 g; 9%) and introducing air at 30° C. under the atmospheric pressure to prepare a solution having an oxygen complex concentration of 0.145 mol/l. Nitrogen gas heated to 80° C. was then passed through the solution, but only oxygen remaining in the gas phase part of the reactor and oxygen physically dissolved in the solution were removed; and no elimination of the combined oxygen from the oxygen complex in the solution was observed, that is, the oxygen absorption reaction was irreversible. This is very advantageous in the aspect of safety in the practical process.

After this operation, cyclopentene (20 ml) was poured into the solution. It could be confirmed by gas chromatography that cyclopentanone (2.1 g) was formed in 30 minutes. Example 51~56

Experiments were carried out as in Example 50 but under conditions indicated in Table 4. The quantities of cyclopentanone formed at 80° C. after 30 minutes are shown in the rightest column of Table 4.

TABLE 4

| Example | CuCl (M) | hmpa (M) | PdCl$_2$ (M) | PhCN (M) | CH$_3$CN (M) | SO$_2$ (sulfolane) (M) | H$_2$O (M) | O$_2$ (M) | T (°C.) | cyclopentanone (g) |
|---|---|---|---|---|---|---|---|---|---|---|
| 51 | 1.0 | 3.9 |  | 0.3 | — | 3.9 | 5.0 | 0.29 |  | 0.92 |
| 52 |  | 0.8 | 0.015 | 1.0 | — |  |  | 0.02 | 80 | 0.03 |
|  | 0.1 |  |  |  |  | 7.6 | — |  |  |  |
| 53 |  | 1.0 |  | — | 1.0 |  |  | 0.02 |  | 0.51 |
| 54 |  |  |  |  |  |  |  | 0.14 |  | 2.9 |
| 55 | 0.2 | 2.8 | 0.045 | — | 6.5 | 1.8 | 5.0 | 0.09 | 50 | 3.5 |

TABLE 4-continued

| Example | CuCl (M) | hmpa (M) | PdCl$_2$ (M) | PhCN (M) | CH$_3$CN (M) | 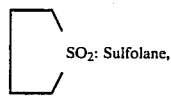SO$_2$ (M) | H$_2$O (M) | O$_2$ (M) | T (°C.) | 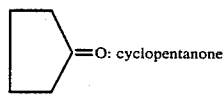=O (g) |
|---|---|---|---|---|---|---|---|---|---|---|
| 56 | | | | | | | | 0.15 | | 2.5 |

 SO$_2$: Sulfolane,

 =O: cyclopentanone

As seen from the above Table, the quantity of cyclopentanone formed in the case of CH$_3$CN addition is greater than that in the case of PhCN addition; the higher the CH$_3$CN concentration, the greater the quantity of cyclopentanone formed; and in the same solution condition, the higher the oxygen concentration, the lower the formation rate of cyclopentanone.

EXAMPLE 57

Experiment was carried out in the same manner as in Example 54 except that the reaction temperature was raised from 50° C. up to 80° C., to obtain 3.2 g of cyclopentanone at a reaction time of 15 minutes.

EXAMPLE 58

Experiment was carried out in the same manner as in Example 54 except that the concentration of Cu(1)Cl was raised from 0.2 M up to 0.5 M, to obtain 3.0 g of cyclopentanone at a reaction time of 20 minutes.

EXAMPLE 59

In Example 54, the quantity of water added was changed to 15 g (3%) to obtain 2.5 g of cyclopentanone in 30 minutes. Further, when the quantity of water added was changed to 88 g (15%), 2.3 g of cyclopentanone was obtained in 30 minutes. In view of this Example and Example 54, it is considered that in the present reaction system, the water content in the vicinity of 9% is optimum. In addition, as shown in Examples 52 and 53, even in the case of a water content of 0%, cyclopentanone is formed to make water separation unnecessary; hence this may often be advantageous as process.

EXAMPLE 60

Experiment was carried out in the same manner as in Example 55 except that Cu(1)Cl (0.2 M) was replaced by Ti(3)CH$_3$ (0.2 M) to obtain 0.61 g of cyclopentanone in 30 minutes.

EXAMPLE 61

Experiment was carried out in the same manner as in Example 55 except that Cu(1)Cl (0.2 M) was replaced by V(3)Cl$_3$ (0.2 M) to obtain 0.72 g of cyclopentanone in 30 minutes.

EXAMPLE 62

Experiment was carried out in the same manner as in Example 54 except that CH$_3$CN was replaced by PhCN to obtain 0.95 g of cyclopentanone at a reaction time of one hour.

EXAMPLE 63

Experiment was carried out in the same manner as in Example 62 except that the concentration of Cu(1)Cl was raised from 0.2 M up to 0.6 M to obtain 1.2 g of cyclopentanone in 30 minutes.

EXAMPLE 64

Experiment was carried out in the same manner as in Example 54 except that 3-methylcyclopentene was poured in place of cyclopentene, to obtain 0.85 g of 1-methyl-3-cyclopentanone

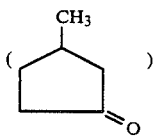

in 30 minutes.

EXAMPLE 65

Into a 100 ml capacity measuring flask were fed Cu(1)Cl (25 g, 0.25 mol) and hmpa (100 g) to prepare a Cu(1)Cl.hmpa complex solution (97 ml). Further, into another 100 ml measuring flask were fed Pd(2)Cl$_2$ (1.3 g, 7.5 mmol) and benzonitrile (hereinafter denoted by PhCN) (15.5 g) and hmpa (60 g) to prepare a Pd(2)Cl$_2$.PhCN hmpa complex solution (74 m(). Both the solutions were then transferred into a 1 capacity reactor, and sulfolane (414 g), was added thereto to prepare a catalyst solution (500 ml) containing 0.5 mol/l of Cu(1)Cl and 0.015 mol/l of Pd(2)Cl $_2$, followed by adding water (49 g, 9%) and introducing air at 30° C. under the atmospheric pressure to prepare a solution having an oxygen complex concentration of 0.145 mol/l, thereafter heating the solution to 80° C. and passing nitrogen gas therethrough, but only oxygen remaining in the gas phase part of the reactor and physically dissolved oxygen were removed, and no elimination of the combined oxygen from the oxygen complex in the solution were observed. After this operation, cyclohexene (20 ml) was poured at 80° C., and as a result it was confirmed by gas chromatography that 2.5 g of cyclohexanone was formed in 30 minutes.

EXAMPLE 66

In Example 65, PhCN was replaced by acetonitrile (CH$_3$CN), to obtain 13.2 g of cyclohexanone in 30 minutes. The results of this experiment show a representative example of the above-mentioned indirect oxidation process, and cyclohexanol was formed in a proportion of 2.5% by weight based on cyclohexanone formed.

EXAMPLE 67

In Example 66, the quantity of water added was made 15 g (3%) to obtain 10.5 g of cyclohexanone in one hour. Further, the quantity of water added was made 88 g (15%) to obtain only 9.8 g of cyclohexanone in 30 minutes. In view of this Example and Example 67, it is considered that in the present reaction system, the optimum water content is in the vicinity of 9%.

EXAMPLE 68

Reaction was carried out in the same manner as in Example 66 except that the concentration of Pd(2)Cl$_2$ was made 0.045 mol/l, to obtain 13.5 g of cyclohexanone in 20 minutes. Further, reaction was carried out raising the concentration of Pd(2)Cl$_2$ up to 0.06 mol/l to obtain 13.6 g of cyclohexanone in 20 minutes, this quantity formed being almost unchanged from that in the case of 0.045 mol/l; thus it was confirmed that in the present invention, it is unnecessary to increase the concentration of Pd(2)Cl$_2$ in vain.

COMPARATIVE EXAMPLE 1

In Example 65, reaction was carried out without adding water to obtain 1.8 g of cyclohexanone in 30 minutes.

COMPARATIVE EXAMPLE 2

In Example 66, reaction was carried out without adding water to obtain 10.9 g of cyclohexanone in 30 minutes. The cyclohexanone yield lowered down to about 80% of the yield in the case of Example 66.

EXAMPLE 69

Experiment was carried out in the same manner as in Example 66 except that in place of hmpa (60 g), ethylene glycol dibutyl ether (50 g) was added as the solvent for the Pd(2)Cl$_2$ (PhCN)2 complex, to obtain 12.8 g of cyclohexanone in 30 minutes.

EXAMPLE 70

Experiment was carried out in the same manner as in Example 66 except that in place of hmpa (60 g), diethylene glycol monomethyl ether (60 g) was added as the solvent for the Pd(2)Cl$_2$.(PhCN)$_2$ complex, to obtain 11.2 g of cyclohexanone in 30 minutes.

EXAMPLE 71

Reaction was carried out in the same manner as in Example 51 except that Cu(1)Cl (50 g, 0.5 mol) was fed and the concentration of the oxygen complex was made 0.290 mol/l, to obtain 19.6 g of cyclohexanone in 20 minutes.

EXAMPLE 72

Reaction was carried out in the same manner as in Example 65 except that in place of hmpa (60 g), PhCN (58 g) was fed as the solvent for the Pd(2)Cl$_2$.(PhCN)$_2$ complex, to obtain 10.7 g of cyclohexanone in 50 minutes.

What we claim is:

1. In the process for producing an oxygen-containing organic compound by oxidizing an olefin in the presence of a metallic complex catalyst, the improvement which comprises utilizing as said metallic complex catalyst, a composite catalyst comprising a metallic complex (MmXnLl) capable of forming an oxygen complex by corrdination thereof with oxygen, a metallic complex (M'M'Xn'L'l') capable of forming an olefin complex by coordination thereof with an olefin, and water, adding an olefin to said metallic complex catalyst mixture to produce an olefin complex by the coordination of said olefin with said metallic complex (M'm'Xn'L'l'), wherein said olefin complex is then oxidized by water to produce an oxygen-containing organic compound, M' and L', and adding an oxygen-containing gas to the metallic complex catalyst mixture to form an oxygen complex by the coordination of said oxygen-containing gas wih said metallic complex (MmXnLl), wherein said oxygen complex is then reacted with M' and L', to produce the metallic complex (M'm'Xn'L'l') utilized in the oxidation reaction, wherein M represents at least one transition metal selected from the group consisting of Cu(1), Ag, Ti(3), Zr, Nb, Cr, Mo, and W; X represents at least one anion selected from the group consisting of Cl$^-$, Br$^-$, I$^-$, BF$_4^-$, PF$_4^-$, CH$_3$COO$^-$, and SO$_4^{2-}$; L represents at least one compound selected from the group consisting of a nitrile and an organic phosphrous compound; L' represents a nitrile; M' represents a transition metal belonging to platinum group VIII of the Periodic Table; m, m', n, and n' represent a number of atoms of said transition metals M and M' and said anions X and X'; respectiely; l and l' represent a number of said ligands L and L' respectively.

2. The process according to claim 1 wherein said organic phosphorous compounds as ligands L are compounds represented by alkoxy, alkyl, or amine derivatives of phosphoric acid or phosphorus acid.

3. The process according to claim 2 wherein said organic phosphourus compounds as ligand L is hexamethylphosphoroamide (hmpa).

4. The process according to claim 1 wherein said m, m', n', l and l', each represent a number in the range of 1 to 4.

5. The process according to claim 1 wherein a basic (electron-donating) compound selected from the group consisting of sulfolane, dimethylsulfolane, dimethlsulfoxide and dimethylformamide is added to a solution of said catalyst.

6. The process according to claim 1 wherein at least one compound selected from the group consisting of alphatic, aromatic or alicyclic hydrocarbons, oxygen-containing organic compounds, organic halogenated compounds, nitrogen-containing compound, organic sulfur compounds, organic fluorine compounds and heterocyclic compounds is used as a solvent for said catalyst.

7. The process according to claim 1 wherein said ligands L or L' are liquids and L or L' are used as a solvent for said complexes.

8. The process according to claim 1 wherein a porous carrier is impregnated with a solution of said metallic complex catalyst, and an olefin and an oxygen-containing gas is contacted with the resulting carrier thereby oxidizing the olefin in the presence of water.

9. The process according to claim 1 wherein said olefin is a linear olefin or a cyclic olefin.

10. The process according to claim 9, wherein said linear olefin is at least one selected from linear olefins having 2 to 8 carbon atoms and said cyclic olefin is cyclopentene or cyclohexene.

11. The process according to claim 1 wherein said nitriles as ligands L and L' are at least one compound selected from the group consisting of benzonitrile and acetonitrile.

12. The process according to claim 1 wherein M is a transition metal selected from the group Cu(1), Ti(3) and V(3).

13. The process according to claim 1 wherein said L is an organic phosphorous compound and said L' is a nitrile.

14. A process for producing an oxygen-containing organic compound by oxidizing an olefin in the presence of a metallic complex catalyst composition comprising the steps of:
   (a) providing a metallic complex catalyst composition comprising a metal complex (M'm'Xn'L'l') capable of forming an olefin complex (M'm'Xn'L'l' .olefin) by coordination thereof with an olefin, a metal complex (MmXnLl) capable of forming an oxygen complex (MmXnLl.$O_2$) by corrdination thereof with oxygen, and water;
   (b) adding an olefin to said metallic complex catalyst composition to produce an olefin complex (M'm'Xn'L'l'.olefin) by the coordination of said olefin with said metal complex (M'm'Xn'L'l'), wherein said olefin complex (M'mXn'L l'.olefin) is then oxidized by water to form an oxygen-containing organic compound and M';
   (c) adding an oxygen-containing gas to the metallic complex catalyst composition to produce an oxygen complex (MmXnLl/$O_2$) by the coordination of said oxygen-containing gas with said metal complex (MmXnLl), wherein, said oxygen complex (MmXnLl.$O_2$) is then reacted with M' and L' to produce the metallic complex (M'mXn'L'l') utilized in the oxidation reaction, wherein M represents at least one transition metal selected from the group consisting of Cu(1), Ag, Ti(3), Zr, Nb, Cr, Mo, and W; X represents at least one anion selected from the group consisting of $Cl^-$, $Br^-$, $I^-$, $BF_4^-$, $PF_4^-$, $CH_3COO-$, and $SO_4^{2-}$; L represents at least one compound selected from the group consisting of a nitrile and an organic phosphorous compund; L' represents a nitrile; M' represents a transition metal belonging to platinum group VIII of the Periodic Table; m, m', n, and n' represent a number of atoms of said transition metals M and M' and said anions X and X' respectively; l and l' represent a number of said ligands L and L'respectively.

15. The process according to claim 14, wherein said organic phosphorus compounds as ligand L are compounds represented by alkoxy, alkyl, or amide derivates of phosphoric acid or phosphorus acid.

16. The process according to claim 14, wherein said organic phosphorus compounds as ligand L is hexamethylphosphoramide (hmpa).

17. The process according to claim 14, wherein said m, m', n, n', and l and l', each represent a number in the group of 1 to 4.

18. The process according to claim 14, wherein the basic (electron donative) compound selected from the group consisting of sulfolane, dimethylsulfolane, dimethylsuloxide, and dimethylformamide is added to the metallic complex catalyst composition.

19. The process according to claim 14, wherein a porous carrier is impregnated with the metallic complex catalyst composition and said olefin and said oxygen-containing gas is placed in contact with the carrier to produce the oxygen-containing organic compound.

20. In the process for producing an oxygen-containing organic compound by oxidizing an olefin in the presence of a metallic complex catalyst composition, the improvement comprises:
   utilizing as said metallic complex catalyst composition, a composite catalyst comprising a metallic complex (Cu(1)Cl.hmpa) capable of forming an oxygen complex by coordination thereof with oxygen, a metallic complex (Pd(2)$Cl_2$.PhCN.hmpa) capable of forming an olefin complex (Pd(2)$Cl_2$.PhCN. olefin) by coordination thereof with an olefin, and water,
   adding an olefin to said metallic complex catalyst composition to produce an olefin complex (Pd(2)$Cl_2$.PhCN.olefin) by the coordination of said olefin with said metallic complex (Pd(2)$Cl_2$.PhCl.hmpa), wherein said olefin complex (Pd(2)$Cl_2$.PhCN.olefin) is then oxidizied by $H_2O$ to produce an oxygen-containing organic compound and Pd(0) and,
   adding an oxygen-containing gas to the metallic complex catalyst composition to form an oxygen complex ((Cu(l)$Cl_2$.hmpa)$_2$.$O_2$) by the corrdination of said oxygen-containing gas with said metallic complex (Cu(1)Cl.hmpa), wherein said oxygen complex ((Cu(1)Cl. hmpa)$_2$.$O_2$) is then reacted with Pd(0) and PhCN to regenerate the metallic complex (Pd(2) $Cl_2$.PhCN.hmpa) utilized in the oxidation reaction.

21. The process according to claim 20 wherein a porous carrier is impregnated with said metallic complex catalyst composition and said olefin and said oxygen-containing gas is placed in contact with the carrier to produce the oxygen-containing organic compound.

* * * * *